United States Patent [19] [11] 4,251,664
Spitzner [45] Feb. 17, 1981

[54] SULFONAMIDOTHIADIAZOLES, METAL COMPLEXES THEREOF, AND SOLUTIONS CONTAINING SUCH COMPOUNDS FOR USE IN EXTRACTION OF METAL VALUES

[75] Inventor: Ernest B. Spitzner, Minneapolis, Minn.

[73] Assignee: Henkel Corporation, Minneapolis, Minn.

[21] Appl. No.: 909,154

[22] Filed: May 24, 1978

[51] Int. Cl.³ .............. C07D 285/12; C22B 15/12; C22B 19/20; C22B 23/00
[52] U.S. Cl. .................... 548/138; 252/184; 423/24; 423/100; 423/139; 548/141
[58] Field of Search .............. 260/306.8 D; 548/138

[56] References Cited

U.S. PATENT DOCUMENTS

| | | | |
|---|---|---|---|
| 2,921,066 | 1/1960 | Worffel et al. | 260/306.8 D |
| 2,980,679 | 4/1961 | Pala | 260/256.5 |
| 3,121,089 | 2/1964 | Jönsson | 260/306.8 D |
| 3,954,936 | 5/1976 | Shozda | 423/24 |
| 4,015,980 | 4/1977 | MacKay et al. | 75/120 |
| 4,051,223 | 9/1977 | MacKay | 423/157 |
| 4,058,585 | 11/1977 | MacKay | 423/24 |
| 4,100,163 | 7/1978 | Virnig | 546/171 |
| 4,128,493 | 12/1978 | MacKay et al. | 252/184 |
| 4,152,396 | 5/1979 | MacKay et al. | 423/139 |
| 4,160,807 | 7/1979 | Virnig et al. | 423/24 |

FOREIGN PATENT DOCUMENTS

| | | | |
|---|---|---|---|
| 212312 | 12/1960 | Austria | 260/306.8 D |
| 1272913 | 8/1961 | France | 260/306.8 D |
| 710614 | 6/1954 | United Kingdom | 260/306.8 D |

OTHER PUBLICATIONS

Bambas, The Chemistry of Heterocyclic Compounds, vol. 4, (Interscience, New York, 1952), pp. 107–108, 114.
Otealeanu et al., Chem. Abstracts, vol. 84, Abstract No. 74145g, (1976).

Primary Examiner—Alton D. Rollins
Attorney, Agent, or Firm—Patrick J. Span

[57] ABSTRACT

Certain sulfonamidothiadiazoles, metal complexes thereof and solutions of said compounds in essentially water-immiscible, liquid hydrocarbon solvents are disclosed. The sulfonamidothiadiazoles have the general structural formula:

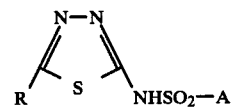

wherein R and A are as defined in the specification and claims hereof. Particular metal values are recovered from their aqueous solutions by using sulfonamidothiadiazoles dissolved in essentially water-immiscible, liquid hydrocarbon solvents. The extraction process involves contacting the metal value containing aqueous solution with the solution of the sulfonamidothiadiazole in essentially water-immiscible, liquid hydrocarbon solvent and stripping the metal from the loaded organic phase.

5 Claims, No Drawings

SULFONAMIDOTHIADIAZOLES, METAL COMPLEXES THEREOF, AND SOLUTIONS CONTAINING SUCH COMPOUNDS FOR USE IN EXTRACTION OF METAL VALUES

The present invention is directed to novel sulfonamidothiadiazoles, organic solvent solutions thereof, metal complexes of such sulfonamidothiadiazoles, organic solvent solutions of such complexes and the method of using said sulfonamidothiadiazoles to extract metal values from aqueous solution.

Liquid ion exchange recovery of metal values from aqueous solutions thereof has in the past ten years or so become a mature commercial operation. Such processing has been described as being deceptively simple since all that is really happening is the transfer of a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities, and (3) engineering application leading to large scale metal recovery.

The key to a successful application of liquid ion exchange is the reagent. In this respect, the reagent should desirably meet a number of criteria. In the first instance, the reagent should complex with or react with a metal or group of metals and such complexing or reaction should be relatively fast in order to avoid having to use large holding tanks or reaction vessels. It is also desirable that the reagent exhibits preference for a single metal where the aqueous starting solutions contain a number of metal values. Such selectivity can often be optimized at designated pH ranges. The reagent should also desirably complex or react quantitatively with the metal under the extraction conditions. Additionally, the reagent, as well as the resulting metal complex, must exhibit satisfactory solubility in the essentially water-immiscible organic solvent being used. Further, the reagent-metal reaction or complexing should be reversible so that the metal can be stripped from the organic phase. For economic reasons, the reagent should be relatively stable so that it can be recycled repeatedly. Also, it should be essentially water insoluble to prevent significant loss into the aqueous phase or phases. Furthermore, the reagent should not cause or stabilize emulsions. Again and principally for economic reasons, the reagent should not react with or load significant quantities of acid, for example, from aqueous acidic stripping solutions. And, of course, the cost of the reagent should be such that the liquid ion exchange process can be operated at a profit.

Of significant, but lesser, importance, is the selection of the essentially water-immiscible solvent to be used in the liquid ion exchange process. Such selection is important principally from a cost standpoint, especially in the recovery of the more common metals. Existing commercial operations for copper recovery, for example, generally employ aliphatic kerosenes because of the low cost thereof. Thus the cost of the reagent and the solvent is intertwined in providing the desired overall economics of the process being commercialized.

One of the most extensively used systems in commercial operation in the last decade for copper recovery has employed benzophenoximes or combination reagents including a benzophenoxime component. While being economic, improvements can be made since the said benzophenoximes do not have total selectivity for copper over iron, for example. Other types of reagents which have been proposed for use in copper recovery such as the alkenyl substituted 8-hydroxyquinolines also have certain drawbacks.

More recently, novel sulfonamidoquinolines which are readily adapted to metal recovery processes employing liquid ion exchange were discovered. These compounds and their metal complexes exhibit the requisite solubility properties which render them of commercial significance in liquid ion exchange processes. Such compounds and their use in metal recovery processes are the subject of co-pending commonly assigned applications Ser. Nos. 843,534, now U.S. Pat. No. 4,209,419 and 845,932, now abandoned. These applications further make reference to low molecular weight sulfonamidoquinolines as reported by Billman and Chernin in Analytical Chemistry, Vol. 34, No. 3, March 1962, pp. 408–410 and U.S. Pat. Nos. 3,268,538 and 3,337,555.

It has now been discovered that certain novel sulfonamidothiadiazoles, as more fully defined hereinafter, are useful in liquid ion exchange recovery processes. The new compounds of the present invention are represented by the followed general structural formula:

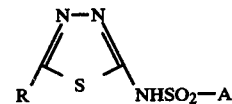

where A is selected from the group of alkyl, aryl, alkaryl and aralkyl and R is selected from the group consisting of alkyl, aryl, alkaryl, aralkyl, mercapto and an alkyl, aryl, alkaryl and aralkyl sulfide. The alkyl groups will generally contain from 1–20 carbon atoms and may be linear or branched chain while the aryl group is generally phenyl. Moreover, it is generally preferred that the compounds of the invention have at least one alkyl group containing eight or more carbon atoms.

The compounds of the present invention are also characterized as having solubilities in essentially water-immiscible liquid hydrocarbon solvents of at least 2% by weight. Correspondingly, they are further characterized in that the copper (Cu++) complexes of the compound have solubilities of at least 2% by weight in the said water-immiscible, liquid hydrocarbon solvents. Especially preferred compounds of the invention are those which exhibit solubilities of at least 2% by weight in both pure and complexed form, in aliphatic or aromatic hydrocarbons, or mixtures thereof, having flash points of at least 150° F. Thus, the compounds of the invention may preferably be further characterized as having substituents containing a sufficient number of carbon atoms and/or branching in the alkyl chains to provide at least the minimum 2% solubility in the aforementioned solvents.

The aforementioned preference for alkyl substituents containing at least 8 carbon atoms and/or possessing a branched chain structure is due to their contribution to the solubilities of the compounds in the above-described solvents. The beneficial effect provided by the number of carbon atoms is obtained by having an alkyl substituent of at least 8 carbon atoms or more than one alkyl substituent in which the sum of the carbon atoms is at least 8. Accordingly, the most preferred compounds of the present invention are those possessing one or more branched chain alkyl substituents having at least 8 carbon atoms or those possessing branched chain alkyl substituents in which the sum of the carbon atoms is at least 8.

According to the preferred embodiments of the present invention, A is preferably the radical

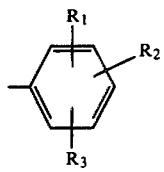

and R is preferably phenyl, mercapto or a benzylsulfide radical of the general structure

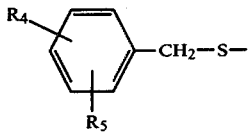

in which $R_1$, $R_2$, $R_3$, $R_4$ and $R_5$, which may be the same or different, are selected from the group consisting of hydrogen and alkyl.

Accordingly, the structural formula for the preferred compounds may be represented as:

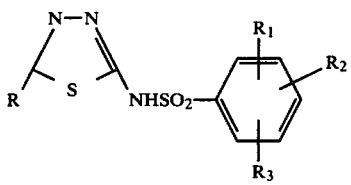

wherein R is selected from the group consisting of phenyl, mercapto, and a benzylsulfide having the structure:

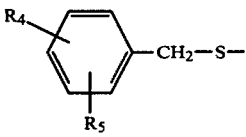

in which $R_1$, $R_2$, $R_3$, $R_4$ and $R_5$, which may be the same or different, are selected from the group consisting of hydrogen and alkyl. Of the numerous compounds which exhibit the preferred solubility characteristics, those in which at least one of $R_1$, $R_2$ and $R_3$ is an alkyl group containing at least 8 carbon atoms, particularly dodecyl are most preferred. However, the preferred effect is also exhibited by compounds in which one or more of the other substituents, i.e., $R_4$ and $R_5$, comprise alkyl groups having eight or more carbon atoms, particularly dodecyl.

Such substituents enhance the compounds' solubilities in essentially water-immiscible, liquid hydrocarbon solvents and hence eliminate the requirement that one of $R_1$, $R_2$ or $R_3$ be an alkyl of sufficient chain length to provide the requisite solubility. Thus, 2-(p-methylbenzenesulfonamido)-5-(dodecylbenzyl)thio-1,3,4-thiadiazole has been found to be particularly effective as a reagent for the extraction of metal values from aqueous solution. It is understood that as the utility of the compounds of the present invention lies in their ability to extract metal values from aqueous solutions, various substituents which do not interfere with chelation may be appended to the aryl or phenyl group without departing from the scope of the invention. Illustrative of such groups are halogen, nitrile, nitro, trifluoromethyl and the like.

The novel compounds of the present invention are prepared from the respective 2-amino-1,3,4-thiadiazoles which have the general structural formula:

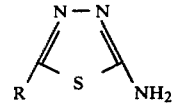

wherein R is as defined above. The amine is dissolved in pyridine and the appropriate alkylbenzenesulfonyl chloride is added slowly with stirring. During this addition, the temperature of the reaction vessel is generally maintained below room temperature. After the introduction of the sulfonyl chloride is complete, the reaction mixture is generally stirred at room temperature for a period ranging from 30 minutes to several hours. Thereafter, the reaction mixture is heated to a temperature below about 70° and 90° C. for an additional time ranging from 30 minutes to several hours after which water is added to the mixture with stirring and continued heating. The reaction mixture is next poured into excess water and the product is recovered via extraction with an organic solvent such as benzene. After extraction, the organic phase is washed several times each with methanolic sodium bicarbonate, followed by brine, a 1 to 10% solution of a mineral acid, e.g., sulfuric or hydrochloric acid, and brine. The remaining organic phase is then dried over magnesium sulfate, filtered and evaporated in vacuo to isolate the sulfonamidothiadiazole product.

The starting materials for the preparation of the compounds of the invention may be prepared (if not commercially available) as follows. The starting 2-amino-1,3,4-thiadiazole is prepared by the general method of K. T. Potts and R. M. Huseby, J. Org. Chem. 31 3528 (1966), involving the reaction of a carboxylic acid of the general structure R—CO$_2$H (R being as defined previously) with thiosemicarbazide in the presence of concentrated sulfuric acid. The starting alkylbenzenesulfonyl chlorides may be prepared from the corresponding alkyl benzene, alkylbenzenesulfonic acid, sodium sulfonate salt or alkyl halide. Further details of the synthesis of the compounds of the invention, including information concerning the starting materials, are found in the Examples which follow the description of the invention.

It is generally difficult to prepare the sulfonamidothiadiazole compounds of the present invention having two large, branched chain substituents on adjacent carbon atoms of aromatic rings of the compounds due to the problem of steric hindrance. Thus, it is preferred that the substituents represented by the various R designations, i.e., $R_1$, $R_2$, $R_3$, $R_4$ and $R_5$, are arranged on the aromatic rings of the compounds of the present invention so as to be on non-adjacent carbon atoms. While this preferred embodiment facilitates preparation of the sulfonamide compounds of the invention, it does not affect the solubility of the compounds in the essentially water-immiscible, liquid hydrocarbon solvents or their ability to extract metal values from aqueous solutions. Thus, sulfonamidothiadiazoles with substituents on vicinal carbon atoms of the aromatic rings, are equally effective as extractants in the process of the invention, although they are more difficult to prepare.

The process of the present invention is a liquid ion exchange process in which any one of the sulfonamidothiadiazole compounds of the invention is dissolved in an essentially water-immiscible, liquid hydrocarbon solvent and the resulting solution is contacted with a metal containing aqueous phase to extract at least a portion of the metal values into the organic phase. The phases are then separated and metal values are stripped from the loaded organic phase by the use of an aqueous stripping medium.

A wide variety of essentially water-immiscible, liquid hydrocarbon solvents can be used in the metal recovery process of the present invention. These include: aliphatic and aromatic hydrocarbons such as kerosenes, benzene, toluene, xylene and the like. The choice of the said essentially water-immiscible liquid hydrocarbon solvent for particular commercial operations will depend on a number of factors including the design of the solvent extraction plant (i.e. mixer-settlers, Podbielniak extractors, etc.), the value of the metal being recovered, disposal of plant effluent and the like. The process of the present invention finds particular use in the extraction recovery of the major, non-ferrous, transition metals—i.e. copper, nickel, zinc, cobalt(II) and cobalt(III), as will be described more fully hereinbelow. Essentially, all of the major plants in operation currently for the recovery of these metals (particularly $Cu++$) use mixer-settlers with relatively large organic inventories and some loss of solvent invariably occurs by evaporation, entrainment in the aqueous and the like. Under these circumstances, preferred solvents for use in the metal recovery processes of the present invention are the aliphatic and aromatic hydrocarbons having flash points of 150° F. and higher and solubilities in water of less than 0.1% by weight. These solvents are also essentially non-toxic and chemically inert and the costs thereof are currently within practical ranges—i.e. normally less than one dollar (U.S.) per gallon to as low as 30¢ (U.S.) or so. Representative commercially available solvents are Kermac 470B (an aliphatic kerosene available from Kerr-McGee—Flash Point 175° F.), Chevron Ion Exchange Solvent (available from Standard Oil of California—Flash Point 195° F.), Escaid 100 and 110 (available from Exxon-Europe—Flash Point ≅180° F.), Norpar 12 (available from Exxon-U.S.A.—Flash Point 160° F.), Conoco C-1214 (available from Conoco—Flash Point 160° F.), Aromatic 150 (an aromatic kerosene available from Exxon-U.S.A.—Flash Point 150° F.) and various other kerosenes and petroleum fractions available from other oil companies.

The present invention thus additionally relates to new compositions wherein the sulfonamidothiadiazole compounds of the invention are dissolved in the essentially water-immiscible, liquid hydrocarbon solvents described above. In this regard, liquid ion exchange reagents are often sold as solutions in organic solvents. These new compositions consist essentially of solutions of at least 2% by weight of the sulfonamidothiadiazoles in essentially water-immiscible, liquid hydrocarbon solvents. When sold as concentrates, the solutions will preferably contain from about 25 to 75% by weight of the sulfonamidothiadiazole.

In the process of the present invention, the organic solvent solutions will preferably contain from about 2 to 75% by weight of the sulfonamidothiadiazole compounds and even more preferably from about 5 to 20% by weight thereof. Additionally, volume ratios of the organic:aqueous phase vary widely since the contacting of any quantity of the sulfonamide solution with the metal containing aqueous phase will result in extraction of metal values into the organic phase. However, for commercial practicality, the organic:aqueous phase ratios are preferably in the range of about 5:1 to 1:5. For practical purposes, the extracting and stripping are normally conducted at ambient temperatures and pressures although higher or lower temperatures and/or pressures are entirely operable. Most advantageously, the entire process can be carried out continuously with the stripped organic solvent solution being recycled for contacting further quantities of metal containing solutions.

The present invention also relates to the metal complexes of the novel sulfonamidothiadiazole compounds and to the essentially water-immiscible, liquid hydrocarbon solvent solutions thereof. The solutions consist essentially of the said solvent and at least 2% by weight, and preferably less than 75% by weight, of the metal complexes. While not normally practiced in the industry, the solutions of the metal complexes can be obtained at one location and transported to another for stripping as hereinafter described. The term "metal complex" as used herein is meant to connote compositions of the novel sulfonamidothiadiazoles with other than insignificant quantities of metal ions. Although the exact structural nature of these complexes has not been ascertained, indications are that under conditions of maximum loading, particularly with $Cu++$ and $Zn++$ metal ions, the complexes comprise the metal and sulfonamide compound generally in a molar ratio of 1:2. Maximum loading, however, is not required for achieving acceptable performance in liquid ion exchange processes and hence the metal complexes are generally defined as including the designated metals in more than insignificant quantities up to maximum loading.

The metal recovery process of the present invention is useful for the recovery of the following metal values from their aqueous solutions: $Cu++$, $Ni++$, $Zn++$, $Co++$ and $Co+++$. These metal values are all transition metals of Groups I b, II b and VIII. The extraction of these various metals from aqueous solutions depends upon a number of factors, including, for example, the concentration of the metal ion, the particular anions present, and the pH of and/or ammonia concentration in the aqueous solutions, as well as the particular sulfonamidothiadiazole chosen and its concentration in the organic phase. Generally, it is preferred to extract the metal values from ammoniacal solutions in which the preferred concentration of ammonia is from about 10 to 150 g/l. However, it is understood that for each aqueous metal solution and sulfonamide reagent solution there will be a preferred or optimum set of extraction conditions, and those skilled in the art, based on the information given herein, especially in the examples to follow, will be able, after a limited number of trial runs, to determine such preferred or optimum conditions for the respective systems under consideration. This is equally true of the stripping operations. By the term stripping is meant the transfer of at least a portion on the metal values in the loaded organic phase to the aqueous stripping medium. The metal values so stripped are desirably recovered from the aqueous stripping medium by conventional techniques, preferably electrolysis. The volume ratios of loaded organic:aqueous stripping phase can also vary widely. However, the overall object of the process is to provide a metal containing stripping solution of known composition and concentration suitable for conventional recovery techniques such as electrolysis. Accordingly, the metal will preferably be present in higher concentrations in the aqueous stripping medium than in the starting metal containing solution. To accomplish this, the loaded organic:aqueous stripping medium phase ratio will normally be in the range of about 1:1 to 10:1. The stripping medium is preferably an aqueous mineral acid solution such as 25 to 250 g/l $H_2SO_4$.

or thermometer, and a condenser. A small portion of water (2 to 10 drops) was added. A solution of the olefin in the remainder of the aromatic hydrocarbon was added slowly with stirring to the reaction vessel. The reaction temperature was maintained somewhere in the range from 0° C. to 50° C. After addition was complete, the reaction mixture was stirred for an additional 15 to 20 minutes while the reaction temperature was maintained. A 10% hydrochloric acid solution (500 ml) was added and the mixture was stirred for 5 minutes. The phases were separated. The organic was washed twice with 2-5% sodium hydroxide, once with brine, and the excess aromatic was stripped off in vacuo. The product was fractionally distilled through a Vigreaux column under vacuum. The ratios of reactants, boiling points, and yields can be found in Table A.

TABLE A

| | | FRIEDEL-CRAFTS ALKYLATIONS | | | | | |
|---|---|---|---|---|---|---|---|
| | | AROMATIC | | | REACTION TEMP | BOILING POINT | YIELD |
| PRODUCT | RUN | HYDROCARBON | OLEFIN | AlCl₃ | °C. | mm of Hg | °C. | % |
| Decyltoluene (Decylmethyl-benzene) | A | Toluene 5m | 1-Decene 1m | 0.05m | 40 | 0.45 | 95-100 | 67 |
| | B | Toluene 10m | 1-Decene 1m | 0.025m | 0-5 | * | 150-155 | 79.9 |
| | C | Toluene 5m | 1-Decene 0.5m | 0.025m | 40 | 0.15 | 80-85 | 73 |
| | D | Toluene 71.4m | 1-Decene 7.6m | 0.357m | 40 | 0.55-0.8 | 106-124 | 76 |

*Water aspirator vacuum

While the process of the present invention has been described as particularly effective in extracting $Cu++$, $Ni++$, $Zn++$, $Co++$ and $Co+++$ metal values from aqueous solutions, it may also be applied to extract other chemically similar metal values, such as $Cd++$, $Hg++$, $Ag+$ and $Pb++$. The process of the invention thus provides a simple, continuous method of extracting valuable metal values from aqueous solutions. Of equal importance is the economic advantages attendant from the process which allows the extracting reagent to be stripped of metal values and recycled for subsequent loading.

To further illustrate the various objects and advantages of the present invention, the following examples are provided. It is understood that their purpose is entirely illustrative and in no way intended to limit the scope of the invention.

EXAMPLE 1

Preparation of Starting Materials

A. Friedel-Crafts Alkylations

The alkylations were carried out via the procedure of Oleson (Ind. Eng. Chem., 52, 833 (1960)).

Approximately one-half to two-thirds of the starting aromatic hydrocarbon and the aluminum chloride were placed in a round bottom three-neck flask fitted with mechanical stirrer, addition funnel, thermocouple well

B. Preparation of the sulfonyl chloride

The sulfonyl chlorides were prepared by two different routes starting from either the alkylbenzene or the alkylbenzenesulfonic acid.

Alkylbenzenesulfonyl chloride from the alkylbenzene

A solution of the alkylbenzene in 1,1,2-trichloroethane (TCE) was cooled to 10° C. and chlorosulfonic acid was added slowly with stirring. The pot temperature was maintained at 10°-15° C. during the addition. After the addition was complete, the reaction mixture was stirred at 10°-15° C. for 15 minutes and then allowed to warm to ambient temperature while stirring for 2-3 hours. The thionyl chloride was added to the stirring reaction mixture. The reaction mixture was heated slowly (1-3 hours) to 90°-120° C. and then held at 90°-120° C. for 30 minutes. A sample was then withdrawn from the reaction mixture. If the presence of the sulfonic acid anhydride was detected by infra-red, an additional mole of thionyl chloride was added and the reaction mixture was stirred at 90°-120° C. for one additional hour. The excess thionyl chloride and TCE were stripped from the reaction mixture in vacuo. The crude sulfonyl chloride was purified by molecular distillation. Ratios of reactants, reaction temperatures, and yields are given in Table B.

TABLE B

| PREPARATION OF ALKYLBENZENESULFONYL CHLORIDES FROM THE ALKYLBENZENE | | | | | | | |
|---|---|---|---|---|---|---|---|
| PRODUCT | RUN | ALKYL-BENZENE (m) | ClSO₃H (m) | SOCl₂ (m) | TCE (ml) | RXN TEMP °C. | DISTILLED YIELD (%) |
| Dodecylbenzenesulfonyl chloride | | 4.34 | 4.34 | 8.68 | 3.67 | 110 | 64 |
| Decyltoluenesulfonyl chloride | A | 5.87 | 5.87 | 11.74 | 500 | 120 | 67 |
| | B | 5.53 | 5.53 | 11.07 | 442 | 110 | 73 |
| | C | 0.25 | 0.275 | 0.55 | 10 | 116 | 56 |

Dodecylbenzenesulfonyl chlorides from the dodecylbenzenesulfonic acids

The sulfonic acid was added slowly over a four-hour period to a stirring solution of thionyl chloride (1 l.) in Skelly C (500 ml). The temperature controller was set for 95° C. and the reaction mixture was heated to reflux. The reaction mixture required approximately two hours to reach 95° C. After stirring at 95° C. overnight, the excess thionyl chloride and Skelly C were stripped off under aspirator vacuum. An additional 50 ml of Skelly C was added and then distilled off under aspirator vacuum to remove the last traces of thionyl chloride. The crude product was then purified by molecular distillation. Amounts of starting acid and yields are given in Table C.

TABLE C

| PRODUCT | CONVERSION OF SULFONIC ACIDS BY THIONYL CHLORIDE | | |
|---|---|---|---|
| | ACID (m) | CRUDE % | DISTILLED (%) |
| dodecylbenzenesulfonyl chloride | 5.82 | — | 94 |

EXAMPLE 2

Synthesis of 2-(Dodecylbenzenesulfonamido)-5-phenyl-1,3,4-thiadiazole

A. Preparation of 2-Amino-5-phenyl-1,3,4-thiadiazole

Starting materials:
  40 gm (0.33 mole) of benzoic acid
  26 gm (0.31 mole) of thiosemicarbazide
  75 ml sulfuric acid (concentrated)

The procedure employed was that described generally by K. T. Potts & R. M. Huseby, J. Org. Chem., 31, 3528 (1966). The concentrated sulfuric acid was placed in a 250 ml three neck flask fitted with a mechanical stirrer, thermometer and condenser. The benzoic acid was then added with stirring. After the benzoic acid was thoroughly mixed, the mixture was cooled in an ice-salt bath and the thiosemicarbazide was slowly added with vigorous stirring. After addition of the thiosemicarbazide was complete, the reaction mixture was removed from the ice bath and allowed to warm to a temperature of 65° C. Thereafter, the reaction mixture was heated to 130° C. and maintained at that temperature for approximately two and one-half hours after which the mixture was cooled to room temperature and allowed to stand overnight. Thereafter the reaction mixture was poured into an ice cold solution of ammonium hydroxide, filtered, and recrystallized from ethanol. 18.6 gm of a white solid was obtained. Nuclear magnetic resonance (NMR) and infra-red (IR) analysis indicated the product of be 2-amino-5-phenyl-1,3,4-thiadiazole with a modest amount of impurity.

B. Preparation of 2-(Dodecylbenzenesulfonamido)-5-phenyl-1,3,4-thiadiazole

Starting materials:
  17.7 gm (0.1 mole) 2-amino-5-phenyl-1,3,4-thiadiazole
  34.4 gm (0.1 mole) of dodecylbenzenesulfonylchloride
  100 ml pyridine The sulfonyl chloride was slowly added to a solution of the thiadiazole in pyridine cooled to 5° C. in an ice bath. The reaction mixture was stirred at room temperature for 2 hours, then heated to 80° C. for one hour. Water was added to the reaction mixture which was continually heated at 80° C. for an additional 30 minutes. Thereafter, the mixture was allowed to cool to room temperature and stand overnight. The reaction product was obtained from the mixture via extraction with benzene. The organic extract was washed several times each with a 2% aqueous $NaHCO_3$ solution containing 25% methanol, brine, a 10% solution of $H_2SO_4$, and brine. The organic phase was then dried over $MgSO_4$, filtered and evaporated in vacuo to give 19.7 gm of a brown waxy solid. IR analysis confirmed the structure of the compound to be that of 2-(Dodecylbenzenesulfonamido)-5-phenyl-1,3,4-thiadiazole.

EXAMPLE 3

Synthesis of 2-(Dodecylbenzenesulfonamido)-5-mercapto-1,3,4-thiadiazole

A. Preparation of 2-amino-5-mercapto-1,3,4-thiadiazole

Starting materials:
  9.3 gm (0.10 mole) thiosemicarbazide
  12 gm (0.16 mole) carbon disulfide
  75 ml pyridine The procedure employed was that generally described by J. Sandstrom, Acta Chem. Scand., 15 1295 (1961). The starting materials were combined and refluxed for two hours. Thereafter, the mixture was evaporated to dryness and the residue was titurated in 75 ml water heated on a steam bath. The resultant mixture was cooled, filtered, washed with cold water and dried in vacuo at 60° C. to give 11.4 gm of a pale yellow solid. NMR and IR analysis indicated the structure to be the desired compound.

B. Preparation of 2-(Dodecylbenzenesulfonamido)-5-mercapto-1,3,4-thiadiazole

Starting materials:
  2.66 gm (0.02 mole) 2-amino-5-mercapto-1,3,4-thiadiazole
  6.9 gm (0.02 mole) of dodecylbenzenesulfonyl chloride
  25 ml pyridine The sulfonyl chloride was slowly added to a solution of the thiadiazole in pyridine and stirred at 80° C. for 20 hours. Thereafter, the reaction mixture was allowed to cool to room temperature and stand overnight. Water was added and the mixture was heated at 80° C. for 30 min. Thereafter, the mixture was cooled to room temperature and the product was obtained by extraction with benzene. The organic extract was washed several times each with a 2% aqueous $NaHCO_3$ solution containing 25% methanol, brine, a 10% solution of $H_2SO_4$ and brine. The organic phase was then dried over $MgSO_4$, filtered and evaporated in vacuo to give 3.0 gm of a clear orange oil. IR analysis confirmed the structure of the compound to be that of 2-(Dodecylbenzenesulfonamido)-5-mercapto-1,3,4-thiadiazole.

EXAMPLE 4

Synthesis of 2-(p-Methylbenzenesulfonamido)-5-(Dodecylbenzyl)thio-1,3,4-thiadiazole

A. Preparation of 2-Amino-5-(Dodecylbenzyl)thio-1,3,4-thiadiazole

Starting materials:
 2.66 gm (0.02 mole) of 2-amino-5-mercapto-1,3,4-thiadiazole
 5.88gm (0.02 mole) of Dodecylbenzylchloride
 3.1 gm (0.022) mole potassium carbonate
 30 ml dimethylformamide The potassium carbonate was added to a solution of the thiadiazole in 20 ml of dimethylformamide and the mixture was heated at 60° C. for 30 min. A white solid was observed. A solution of the dodecylbenzyl chloride in 10 ml of dimethylformamide was then slowly added with stirring at a temperature of 60° C. The reaction mixture was continuously heated for approximately 4 hours after which it was allowed to cool to room temperature and stand overnight. The reaction product was recovered by extraction with benzene. The benzene extract was washed several times with brine, dried over $MgSO_4$, filtered and evaporated in vacuo to give 6.1 gm of a tan, gummy substance. NMR and IR analysis confirmed the structure of the compound to be 2-amino-5-(p-dodecylbenzyl)thio-1,3,4-thiadiazole.

B. Preparation of 2-(p-methylbenzenesulfonamido)-5-(Dodecylbenzyl)thio-1,3,4-thiadiazole Starting materials:
 5.9 gm (0.014 mole) of 2-amino-5-(Dodecylbenzyl)thio-1,3,4-thiadiazole
 2.9 gm (0.015 mole) p-methylbenzenesulfonyl chloride
 20 ml pyridine The p-methylbenzenesulfonyl chloride was slowly added to a solution of the thiadiazole in pyridine cooled to 5° C. in an ice bath. The reaction mixture was warmed to room temperature and stirred for two hours, then heated to 80° C. for one hour. Water was added to the mixture which was continuously heated at 80° C. for an additional 30 minutes. Thereafter, the mixture was allowed to cool to room temperature and stand overnight. The product was recovered by extraction with benzene. The benzene extract was washed several times each with a 2% aqueous $NaHCO_3$ solution containing 25% methanol, brine, a 10% sulfuric acid solution and brine. The clarified organic phase was then dried over $MgSO_4$, filtered and evaporated in vacuo to give 5.6 gm of a viscous red syrupy substance. NMR and IR analysis confirmed the structure of the product to be 2-(p-methylbenzenesulfonamido)-5-(dodecylbenzyl)thio-1,3,4-thiadiazole.

EXAMPLE 5

Extraction of Metal Values

To determine the ability of the various sulfonamidothiadiazole compounds of the present invention to extract metal values from aqueous solutions, tests were conducted in accordance with the following procedures.

A 0.1 mole solution of the sulfonamide compound in an identified essentially water-immiscible liquid hydrocarbon solvent and five aqueous solutions of the following compositions were used:

| Metal | Composition |
| --- | --- |
| $Cu^{++}$ | 0.05 M $CuSO_4$ (3.2 g./l. $Cu^{++}$), 0.4 M $NH_3$, and 0.1 M $(NH_4)_2SO_4$ |
| $Ni^{++}$ | 0.05 M $NiSO_4$ (2.9 g./l. $Ni^{++}$), 0.4 M $NH_3$, and 0.1 M $(NH_4)_2SO_4$ |
| $Zn^{++}$ | 0.05 M $ZnSO_4$ (3.2 g./l. $Zn^{++}$), 0.4 M $NH_3$, and 0.1 M $(NH_4)_2SO_4$ |
| $Co^{++}$ | 0.025 M $CoSO_4$ (1.5 g./l. $Co^{++}$), 1.7 M $NH_3$, and 0.1 M $(NH_4)_2SO_4$ prepared as needed under an atmosphere of nitrogen |
| $Co^{+++}$ | 0.025 M $CoSO_4$ (1.5 g./l. $Co^{++}$), 1.7 M $NH_3$, and 0.1 M $(NH_4)_2CO_3$ (air oxidized to $Co^{+++}$) |

Portions of the organic solution were shaken with the five aqueous solutions at an organic:aqueous phase volume ratio of 1:1 for one hour at ambient temperature. The organic phases were then analyzed for metal content. If a third phase was present, both the organic and aqueous phases were clarified and analyzed. Table D summarizes the data obtained from the extraction tests for various sulfonamidothiadiazole reagents of the present invention.

TABLE D

| REAGENT | SOLVENT | $[Cu^{++}]$ org. | $[Ni^{++}]$ org. | $[Co^{++}]$ org. | $[Co^{+++}]$ org. | $[Zn^{++}]$ org. |
| --- | --- | --- | --- | --- | --- | --- |
| 2-(Dodecylbenzenesulfonamido)-5-phenyl-1,2,3-thiadiazole | Solvesso* 150 | 0.510 | 1.94 | — | 1.40 | 2.07 |
| 2-(Dodecylbenzenesulfonamido)-5-mercapto-1,3,4-thiadiazole | Solvesso | 1.90 | 1.25 | 0.940 | 0.905 | 0.980 |
| 2-(p-Methylbenzenesulfonamido)-5-(dodecylbenzyl)thio-1,2,3,4-thiadiazole | Solvesso 150 | 1.82 | 2.40 | — | 1.10 | 1.96 |

All concentrations are given in grams per liter.
*Solvesso 150 is an aromatic kerosene having a flash point of 150° F. (see, Zimmerman & Lavine, Handbook of Material Trade Names, 1953 Ed., p. 523.)

EXAMPLE 6 pH Isotherms

To determine the extent of extraction of various metal ions as a function of pH, tests were conducted as follows. Portions of a 0.1 molar solution of a particular sulfonamidothiadiazole in an identified essentially water-immiscible liquid hydrocarbon solvent were shaken with aqueous solutions composed of equivolumes of the following components:

Component A—0.2 M metal sulfate solution in water
 Component B—water or sulfuric acid or sodium hydroxide solutions ranging from 0.01 to 0.1 M Component B was selected in such a manner as to ensure the desired pH of the aqueous raffinate. In each test, the organic solution and aqueous solution were shaken at an organic:aqueous phase volume ratio of 1:1 for one hour at ambient temperature. Subsequent analysis of the organic phase for metal content and the aqueous phase for pH generated the data contained in Table E which demonstrates the degree of metal extraction as a function of pH for the particular reagent system under study. In the table concentrations are given in grams per liter unless otherwise indicated.

TABLE E

| 2-(Dodecylbenzenesulfonamido)-5-phenyl-1,3,4-thiadiazole in Solvesso 150 | | | | | | | | | |
|---|---|---|---|---|---|---|---|---|---|
| Cu | AQ pH | Ni | AQ pH | $Co^{+2}$ | AQ pH | Zn | AQ pH | $Fe^{+3}$ | AQ pH |
| 0.024 | 0.6 | <0.005 | 0.61 | <0.005 | 0.63 | <0.005 | 0.61 | <0.005 | 0.57 |
| 0.035 | 1.31 | 0.007 | 1.33 | <0.005 | 1.34 | <0.005 | 1.33 | <0.005 | 1.16 |
| 0.310 | 3.13 | 0.415 | 4.92 | 0.350 | 5.38 | 0.620 | 5.32 | 0.008 | 1.74 |
| 0.440 | 3.46 | 1.10 | 5.55 | 0.970 | 6.05 | 1.18 | 5.83 | | |
| 1.11 | 4.13 | | | | | | | | |
| 2.21 | 4.53 | | | | | | | | |

EXAMPLE 7

Ammonia Isotherms

To determine the extent of extraction of various metal ions as a function of total ammonia concentration in the aqueous phase, tests were conducted in accordance with the following procedure. Portions of a 0.1 molar solution of 2-(Dodecylbenzenesulfonamido)-5-phenyl-1,3,4-thiadiazole in Solvesso 150 solvent were shaken at 1:1 organic:aqueous phase volume ratio for approximately one hour at ambient temperature with aqueous ammoniacal solutions containing a particular metal ion. The organic phase was then separated and analyzed for metal concentration, generating the data contained in Tables F-I which demonstrate the degree of metal extraction as a function of ammonia concentration for the particular reagent system. In the tables all concentrations are given in grams per liter.

EXAMPLE 8

Acid Stripping, Ammonia Loading and Acid Loading

In order to determine (1) the extent of metal stripping as a function of acid concentration, (2), the extent of ammonia loading during extraction and (3) the extent of acid loading during stripping, the following tests were conducted. A 0.1 M solution of 2-(Dodecylbenzenesulfonamido)-5-phenyl-1,3,4-thiadiazole in Solvesso 150 and aqueous solutions having the following compositions were prepared:

A. a 0.1 M metal sulfate, 0.6 M $NH_3$ and 0.15 M $(NH_4)_2SO_4$ solution in water.
B. a 100 gpl $H_2SO_4$ solution in water.

In the first step, the reagent solution was shaken with aqueous solution A at an organic:aqueous phase volume ratio of 1:2 for one hour at ambient temperature. The phases were separated and the loaded organic phase was contacted a second time as before with fresh aqueous solution A. The resulting organic phase was separated and analyzed for metal concentration. The loaded organic phase was then shaken with solution B at an organic:aqueous phase ratio of 1:1 for one hour at ambient temperature. The phases were then separated and the organic was analyzed for metal content while the aqueous phase was analyzed for ammonia concentration. Next, the stripped organic phase was washed with water at an organic:aqueous phase ratio of 1:1 for one hour and analyzed for $H_2SO_4$ concentration. The results of this procedure are disclosed in Table J.

TABLE F

| [$NH_3$] Aq. Feed | [Cu] Aq Feed | [Cu] org. | % Extraction |
|---|---|---|---|
| 15.1 | 0.316 | 0.312 | 99 |
| 29.9 | 0.311 | 0.275 | 88 |
| 55.4 | 0.316 | 0.216 | 68 |
| 85.1 | 0.314 | 0.145 | 46 |
| 104.0 | 0.320 | 0.093 | 29 |
| 141.9 | 0.343 | 0.068 | 20 |

TABLE G

| [$NH_3$] Aq. Feed | [Ni] Aq Feed | [Ni] org. | % Extraction |
|---|---|---|---|
| 15.1 | 0.347 | 0.289 | 83 |
| 30.0 | 0.357 | 0.290 | 81 |
| 60.0 | 0.359 | 0.250 | 70 |
| 89.5 | 0.369 | 0.198 | 54 |
| 118.6 | 0.378 | 0.145 | 38 |
| 149.6 | 0.374 | 0.100 | 27 |

TABLE H

| [$NH_3$] Aq. Feed | [Co] Aq Feed | [Co] org. | % Extraction |
|---|---|---|---|
| 14.7 | 0.305 | 0.250 | 82 |
| 29.7 | 0.303 | 0.259 | 84 |
| 56.7 | 0.302 | 0.225 | 75 |
| 77.6 | 0.301 | 0.185 | 61 |
| 102.6 | 0.309 | 0.137 | 44 |
| 129.2 | 0.294 | 0.110 | 37 |

TABLE I

| [$NH_3$] Aq. Feed | [Zn] Ag. Feed | [Zn] org. | % Extraction |
|---|---|---|---|
| 14.4 | 0.330 | 0.333 | 100 |
| 28.9 | 0.332 | 0.306 | 92 |
| 58.3 | 0.332 | 0.185 | 56 |
| 87.2 | 0.332 | 0.110 | 33 |
| 116.2 | 0.331 | 0.068 | 21 |
| 147.0 | 0.331 | 0.024 | 13 |

TABLE J

| Ni | |
|---|---|
| Ni - organic before strip (gpl) | 2.80 |
| Ni - organic after strip (gpl) | 0.005 |
| % Stripping | 100 |
| $NH_3$ AQ Strip (gpl) | 0.68 |
| pH AQ Scrub | 3.68 |
| Zn | |
| Zn - organic before strip (gpl) | 3,28 |
| Zn - aqueous after strip (gpl) | 3.44 |
| % Stripping | 100 |
| $NH_3$ AQ Strip (gpl) | 1.87 |
| pH AQ Scrub | 3.68 |

While the invention has now been described in terms of various preferred process parameters, and exemplified with respect thereto, the skilled artisan will appreciate that various substitutions, changes, omissions, and modifications may be made without departing from the spirit thereof. Accordingly, it is intended that the scope of the invention be limited solely by that of the following claims.

The embodiments of the invention in which an exclusive property or privilege is claimed are defined as follows:

1. Compounds of the structure:

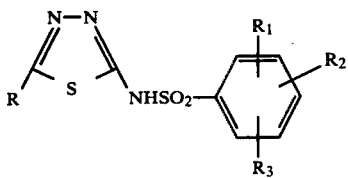

wherein R is phenyl in which $R_1$, $R_2$, and $R_3$, which may be the same or different, are selected from the group consisting of hydrogen and linear and branched chain alkyl containing from 1 to 20 carbon atoms, said compounds being further characterized as having solubilities of at least 2% by weight in essentially water-immiscible, liquid hydrocarbon solvents.

2. The compounds of claim 1, wherein said liquid hydrocarbon solvent is selected from the group consisting of aliphatic and aromatic hydrocarbons and mixtures thereof having flash points of at least 150° F. and further characterized in that the $Cu++$ complexes thereof also have solubilities of at least 2% by weight in said liquid hydrocarbon solvents.

3. The compounds of claim 1, wherein at least one of $R_1$, $R_2$ and $R_3$ is a linear or branched chain alkyl containing at least eight carbon atoms.

4. The compounds of claim 1, wherein one of $R_1$, $R_2$ and $R_3$ is dodecyl.

5. 2-(dodecylbenzenesulfonamido)-5-phenyl-1,3,4-thiadiazole.

* * * * *

UNITED STATES PATENT AND TRADEMARK OFFICE
CERTIFICATE OF CORRECTION

PATENT NO. : 4,251,664
DATED : 02/17/81
INVENTOR(S) : Ernest Spitzner

It is certified that error appears in the above-identified patent and that said Letters Patent are hereby corrected as shown below:

In column 4, line 28; "below" should read -- between --.

In column 12, Table D, line 2 under REAGENT; "5-phenyl-1,2,3-" should read -- 5-phenyl-1,3,4- --.

In column 12, Table D, line 6 under REAGENT, "1,2,3,4-" should read -- 1,3,4- --.

In column 14, Table I; under [Zn], instead of "Ag. Feed", it should read -- Aq. Feed --.

Signed and Sealed this

Nineteenth Day of March 1985

[SEAL]

Attest:

DONALD J. QUIGG

Attesting Officer

Acting Commissioner of Patents and Trademarks